(12) United States Patent
Gergel et al.

(10) Patent No.: US 6,225,799 B1
(45) Date of Patent: May 1, 2001

(54) METHOD AND APPARATUS FOR TESTING MAGNETIC HEADS AND HARD DISKS

(76) Inventors: Oleg A. Gergel, 2245 Latham St. #24, Mountain View, CA (US) 94040;
Mostafa Mahmoudian, 89 Club Dr., San Carlos, CA (US) 94070

( * ) Notice: Subject to any disclaimer, the term of this patent is extended or adjusted under 35 U.S.C. 154(b) by 0 days.

(21) Appl. No.: 09/197,745

(22) Filed: Nov. 23, 1998

(51) Int. Cl.$^7$ ............................. G01N 19/02; G11B 21/22
(52) U.S. Cl. ................................ 324/212; 73/9; 360/75; 360/137; 360/78.11
(58) Field of Search ................................ 324/210, 212; 73/9; 360/75, 78.11, 75.03, 137

(56) References Cited

U.S. PATENT DOCUMENTS 5,115,644 * 5/1992 Hegde et al. ............................. 73/9
5,455,723 * 10/1995 Boutaghou et al. .................... 360/75

* cited by examiner

Primary Examiner—Walter E. Snow
(74) Attorney, Agent, or Firm—I. Zborovsky

(57) ABSTRACT

A method and apparatus for start-stop testing magnetic heads and hard disks in real disk-drive environment is provided. The tester has essentially the same dimensions as a conventional disk drive so that rotation of the disk pack inside the tester housing generates the same aerodynamic conditions as in a real disk drive. An accurate head positioning system, the operation of which does not depend on the deterioration of the magnetic conditions of the head and disk, is located inside the tester housing, and the friction and sticking forces can be measured till the moment of physical crash inside the housing. An essential advantage of the tester of the invention in that the measurement and positioning systems are combined into a single unit. The aforementioned combined system is based on the use of a Hall-effect sensor attached to the voice coil of the type used in the disk drive. Friction forces between the magnetic heads and the disks are measured by utilizing a voltage applied to the voltage-to-current converter.

22 Claims, 3 Drawing Sheets

METHOD AND APPARATUS FOR TESTING MAGNETIC HEADS AND HARD DISKS

FIELD OF THE INVENTION

The present invention relates to the field of magneic recording, in particular to a method and apparatus for start-stop testing magnetic heads and hard disks. The invention may find application in testing properties and measuring characteristics of disk packs used in computer disk drives.

BACKGROUND OF THE INVENTION

Prior to installation into computer disk drives, magnetic disks or a set of disks combined into so called disk pack has to be tested with respect to their basic characteristics such as a signal-to-noise ratio, track-to-track error, sticking of the head to the disk surface at starting of disk rotation, friction between the magnetic head and the surface of the magnetic medium, etc. The tests which are aimed specifically at testing and measuring aforementioned friction and rotation starting characteristics are known as start-stop tests.

In order to better understand the principle of the present invention, it would be useful to explain in a simplified form the construction and principle of operation of a conventional hard disk drive. A hard disk drive consists of a housing which contains a spindle motor which rotatingly supports a disk or a disk pack. The housing also supports a head or a head stack which is secured on a pivotally supported arm capable of performing swinging motions so that the magnetic head or heads can scan the working surfaces of the disk or disks for writing or reading the information recorded on the disk/disks. The arm is driven and positioned by means of a so called voice coil motor which in fact is an electric linear motor. The disks are rotated with a high speed. Each magnetic disk has to concentric zones. i.e., a head loading zone and a working zone. When the disk drive is switched into operation, the disk begin to rotate, and the pivot arm is positioned over the head loading zone. The latter has a plurality of microscopic projections for reducing the friction and sticking force between the magnetic head and the disk surface. The rotation speed of the disk increases to the level at which an air cushion is formed between the head and the disk sufficient to support the head out of physical contact with the disk surface, the pivot arm with the magnetic head is shifted further to the working zone of the disk where appropriate read/write operations are performed. Upon completion of the working cycle of the disk drive, the pivot arm returns the magnetic head to the parking position over the loading zone.

The information is recorded on the disks in the form of magnetic signals arranged on concentric tracks. In order to ensure recording of large volume of information, the magnetic signals are recorded with a very high density, and tolerances or track-to-track distances are very tight, e.g., on the order of ±0.012 μm. It is understood that under these conditions the magnetic head should be very accurately positioned over appropriate tracks, and this function is fulfilled by means of servo signals prewritten on the disks for forming aforementioned tracks. This is so-called disk-formatting operations with which all computer users are familiar when working with non-formatted floppy disks.

Multiple start-stop operations of the disk drive cause deterioration of the magnetic-medium surfaces of the disks as well as the working surfaces of the magnetic heads. In the disk drives the disks rotate in a confined space limited by strict requirements to the overall dimensions of the disk drive. Therefore the products of wear such as debris from the deterioration of the disks and heads are accumulated inside the disk drive housing and contaminate the working surfaces. Eventually these particles penetrate the read/write gap and may further operation of the disk drive impossible.

Therefore, it is extremely important to test start-stop characteristics of the magnetic heads and magnetic disks inside the disk drive housings.

Start-stop testers for testing friction characteristics and sticking properties in head-disk pair are known in the art. For example, Center for Tribology, Inc, Mountain View, Calif. has developed a start-stop (Model. HDI Reliability Test System [RTS]). This tester has base plate which supports a spindle-motor unit for rotation of a hard disk to be tested and an additional electric motor for swinging motions of an arm which supports a magnetic head. A strain gauge is attached to the point of connection between the head and head-supporting structure for measuring the friction and sticking forces generated between the head and the disk during testing. The tester is equipped with a measurement system for measuring aforementioned forces, number of working cycles, etc.

A main disadvantages of this tester is that the disk is tested in an environment different from that inside the disk drive housing an that the products of wear and deterioration are removed from the zone of contact between the head and the disk and therefore do not affect their performance characteristics. The known start-stop testers utilize various systems for accurate positioning of the magnetic head with respect to tracks of the hard disk. For example, it may be an external (i.e., located outside the disk drive) positioning system with the use of a stepper motor which has low positioning accuracy. For example, even with the use of a special gear mechanism, the accuracy of the stepper-motor positioning system cannot be better than 1 μm. Other testers utilize optical encoders such as a standard device (Model LIP401R), produced, e.g., by Heidenhain Corporation, Schaunburg, Ill., USA. Although the optical encoders may provide high positioning accuracy, they are heavy and large in size.

The start-stop tests are carried out till the crash conditions, i.e., to the conditions at which further read/write operation becomes impossible. In order to monitor the head and the magnetic medium deterioration, the read/write operation should be performed after each start-stop cycle.

Another disadvantage of conventional start-stop head/disk testers is that they are capable of measuring friction and sticking forces only for a single magnetic head. This is because the friction and sticking forces are measured by means of a strain gage located at the point of connection of the head to the pivot arm. In other words, these testers are not applicable for testing friction and sticking characteristics of the head stacks as a unity.

Furthermore, the known testers require that separate measurement and positioning systems be used for measuring head/disk characteristics and or accurate positioning of the head with the respect to the disk tracks.

On the other hand, in a real disk drive the disk, which rotates with a very high speed of about 4000 to 10000 rpm or more, generates aerodynamic conditions which cannot be neglected and which exert an influence on the formation of the air gap, resistance to disk rotation, etc. An ideal condition would be if the start-stop test is conducted inside the disk drive. This condition, however, cannot be implemented in view of the large dimensions and heavy weight of the external positioning mechanisms. In case the actual head positioning mechanism of the disk drive is used for this purpose, it would be impossible to continue the test, since deterioration of measurement conditions anticipate the actual physical deterioration of the working head and disk surfaces. In other words, when the measurement conditions are deteriorated because of contamination of the track surfaces and of the head gap to the extent that further measurement is impossible, it also becomes impossible to obtain any data which occurs at he moment of physical crash of the aforementioned components of the tester.

OBJECTS OF THE INVENTION

It is an object of the invention to provide a method and apparatus for start-stop testing magnetic heads and hard disks in real disk-drive environment. Another object of the invention is to provide an apparatus for start-stop testing of magnetic heads and disks inside a housing of the tester which reproduces the same aerodynamic conditions for a disk rotating with a high speed as in the housing of a real disk drive. Still another object of the invention is to provide an accurate head positioning device which can fit into the tester housing which has the same dimensions as a real disk drive. Further object is to provide a measurement system for the head/disk tester of the aforementioned type which allows measurement of friction and sticking forces till the moment of physical crash. Another object is to provide a start-stop tester for testing friction and sticking characteristics of a head stack as a unity. Still another object is to provide a tester of the aforementioned type in which the test may be conducted till physical crash irrespective of the deterioration of the magnetic conditions of head and disk. An additional object of the invention is to provide a combined measurement and positioning system which measures characteristics of the heads and disks and ensures accurate positioning of the head with respect to the disk tracks.

SUMMARY OF THE INVENTION

A method and apparatus for start-stop testing magnetic heads and hard disks in real disk-drive environment are provided. The tester has essentially the same dimensions as a conventional disk drive so that rotation of the disk pack inside the tester housing generates the same aerodynamic conditions as in a real disk drive. An accurate head positioning system, the operation of which does not depend on the deterioration of the magnetic conditions of the head and disk, is located inside the tester housing, and the friction and sticking forces can be measured till the moment of physical crash inside the housing. An essential advantage of the tester of the invention in that the measurement and positioning systems are combined into a single unit.

DETAILED DESCRIPTION OF THE PREFERRED EMBODIMENT OF THE INVENTION

The method of the invention consists in providing a start-stop tester which has a housing and a mechanical part, i.e., a voice coil and a pivot arm which supports the magnetic head identical to a real disk drive, providing the voice coil with a Hall-effect sensor which interacts with the permanent magnet of the voice-coil motor assembly, placing the object being tested into the aforementioned housing, positioning the magnetic head into a required position on the disk, starting rotation of the disk with the head resting on its surface thus developing a friction force between them, and measuring the aforementioned friction force with the use of the Hall-effect sensor.

Figure 1:
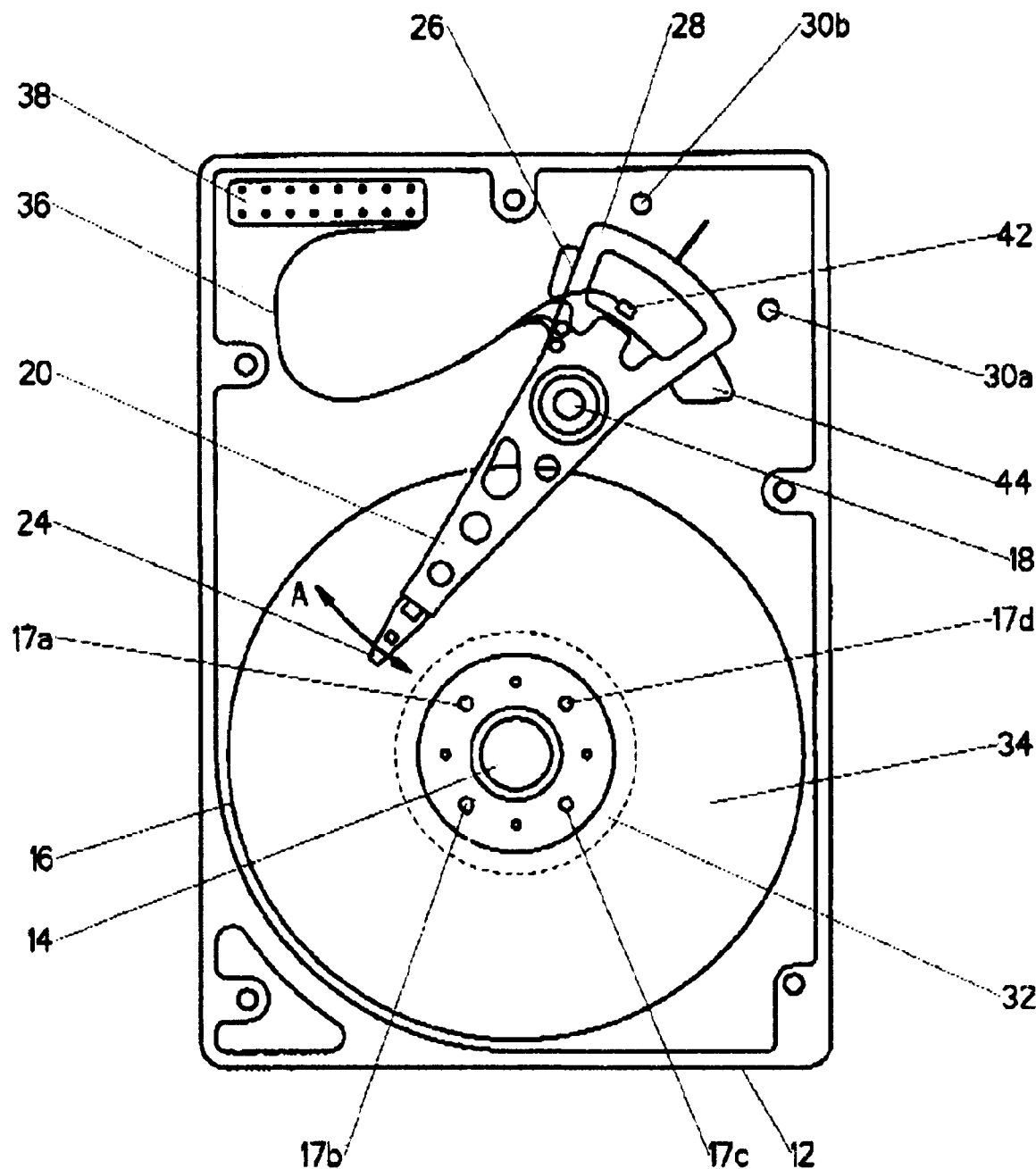
FIG. 1 is a top view of a head/disk start-stop tester of the invention with the upper cover of the tester housing removed, the relationship between the components being shown in proportions close to real.
Figure 2:
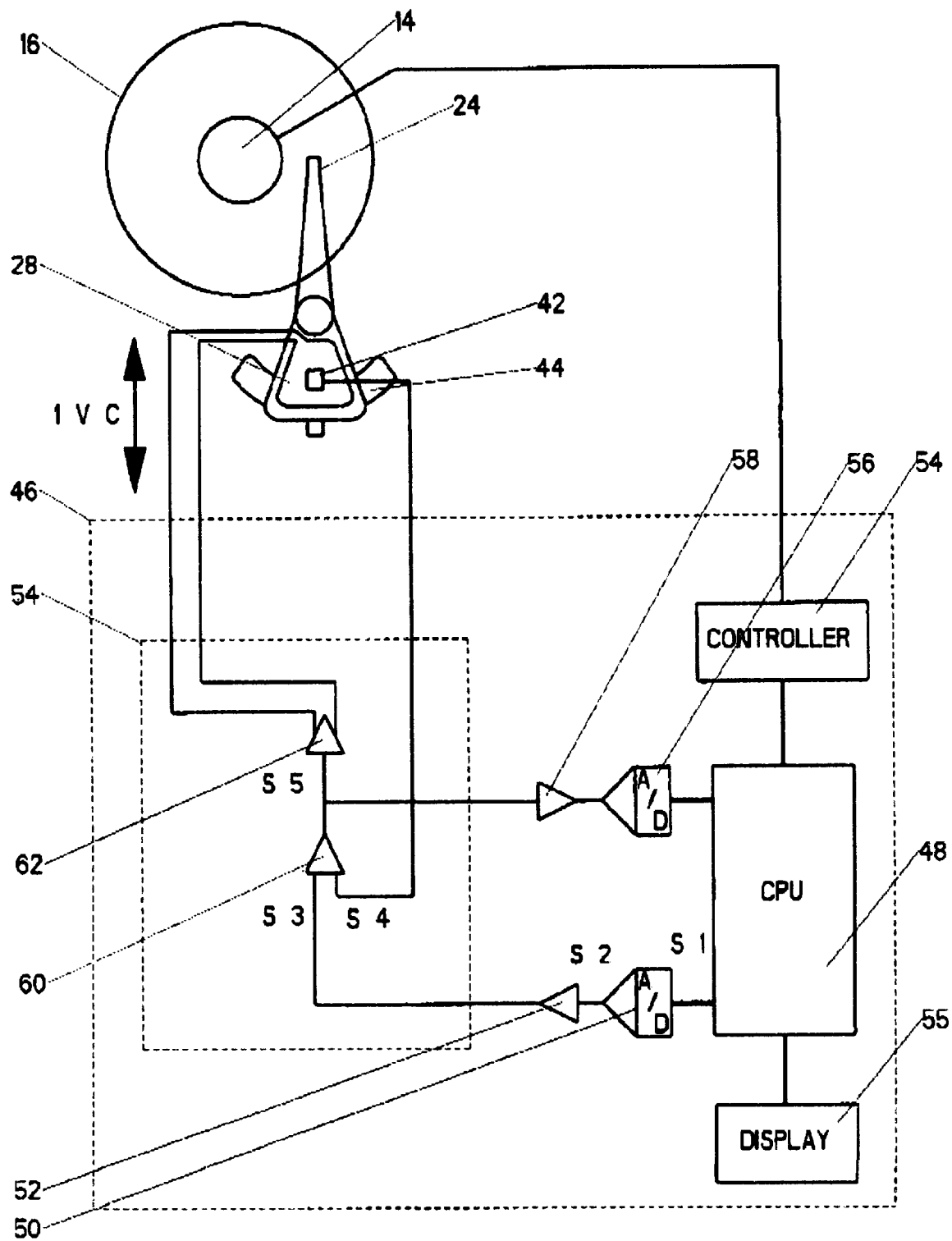
FIG. 2 is a schematic representation of the tester with mechanical and electrical components, partially in a block-diagram form.
Figure 3:
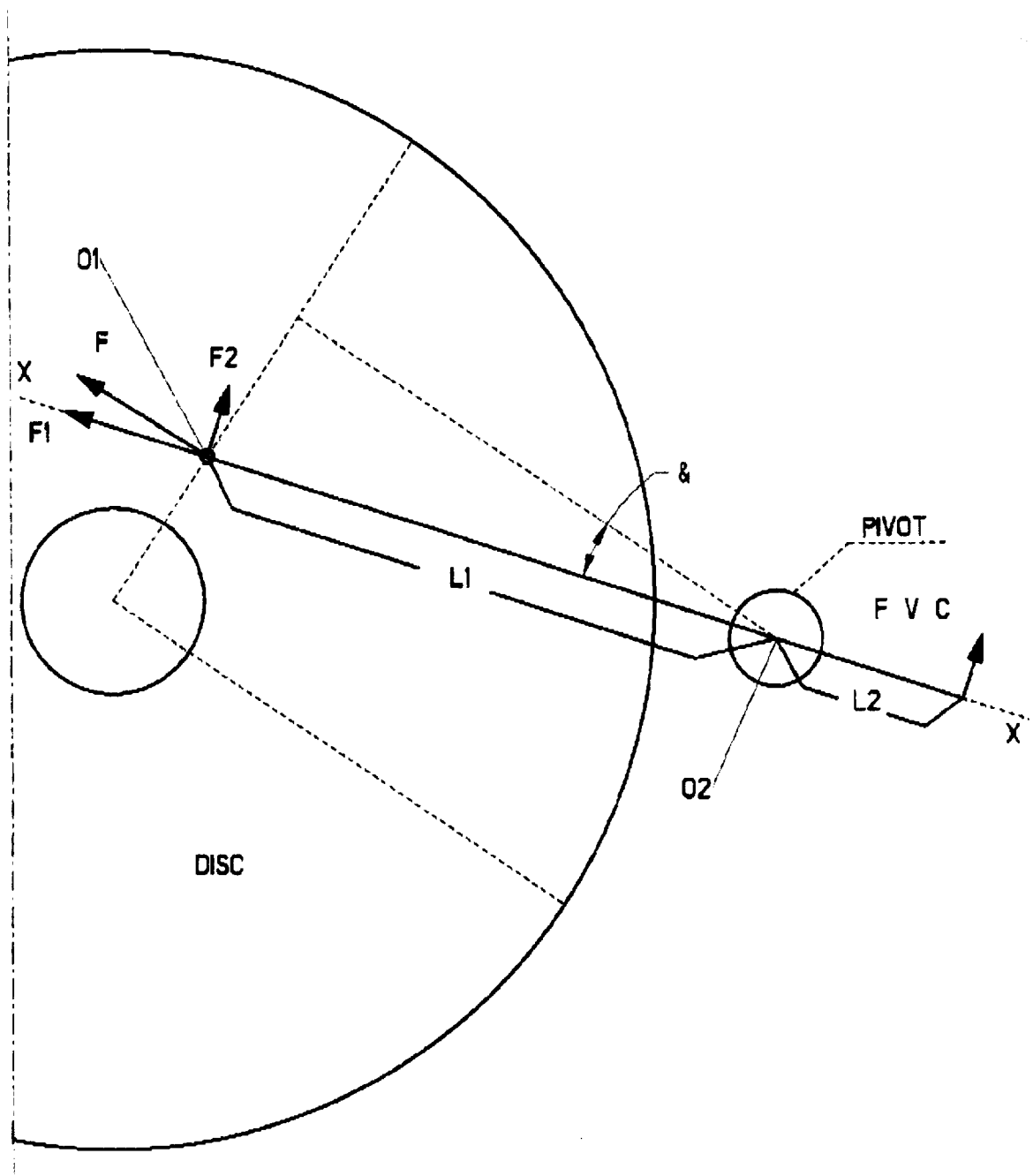
FIG. 3 is a schematic view illustrating friction forces developed between the magnetic head and magnetic disk in the start-stop tester of the invention.

The method of the invention can be carried out with the use of a start-stop tester of the invention which is shown and described with references to FIGS. 1 through 3.

FIG. 1 is a top view of a head/disk start-stop tester 10 of the invention with the upper cover of a tester housing 12 removed, the relationship between the components being shown in proportions close to real. In a normal operative condition, housing 12 of the tester is closed and sealed. Installed inside housing 12 is a spindle-motor unit 14 which supports a disk pack 16 to be rotated with a high speed corresponding to the speed of rotation of a disk pack in a real disk drive. For example, disk pack 16 may be rotated during testing with a speed within the range of 4000 to 10000 rpm or higher. It is understood that disk pack 16 consists of a plurality of magnetic disks 16a, 16b . . . 16n which are spaced from each other for interaction with a plurality of respective magnetic heads mentioned below. Only disk 16a is shown and will be referred to in the subsequent description for the simplicity of explanation, but it is understood that a plurality of disks can be tested at the same time in start-stop tester of the invention. Disk pack 16 is secured on the spindle of spindle-motor unit 14, e.g., by means of a washer 15 which is placed on the top of the disk pack and screws 17a, 17b, 17c, and 17d which press washer 15 down against upper disk 16a of the pack.

Installed on a separate axis of rotation 18 inside housing 12 is a pivot arm 20 which has a longer portion 22 which projects radially inwardly toward the center of disk pack 16 and supports on its tip a magnetic read/write head 24 and a shorter portion 26 which supports a so-called voice coil 28. Longer portion 22 of pivot arm performs swinging motions in the direction shown by an arrow A to overlap in its motion all the tracks of disk 16a. The angular range of movements of pivot arm is limited by hard stops 30a and 30b. It is understood that in accordance with a conventional technique, magnetic head 24 slides over the surface of disk 16a which rotates with a very high speed with the formation of an air cushion formed between disk 16a and magnetic head 24. The air cushion normally has a thickness of about 0.025 to 0.25 $\mu$m and support magnetic head without physical contact with the magnetic medium on the surface of disk 16a. Magnetic disk 16a has a loading zone 32 and working zone 34. The function of these zones is the same as has been described above in connection with the prior art. The same relates to voice coil 28 which function as a linear motor for rotating pivot arm 20. Reference numeral 36 designates lead wires for energizing voice coil 28. The output ends of lead wires 36 are attached to an electric connector 38 or connection to an external electronic unit 40.

With the exception that electronic unit 40 is different, the parts and units of start-stop tester 10, which have been described to this points, are similar in their construction, shape, and dimensions to those used in a conventional computer disk drive. It is also understood that disk pack 16 and/or magnetic head 24 shown in FIG. 1 are not parts of start/stop tester 10 but objects to be tested. More specifically, if an object to be tested is disk pack 16, magnetic heads 24 are inherent in the tester, and if magnetic heads are objects of the test, disk 16a or disk pack 16 belongs to the tester.

Although the mechanical part of start-stop tester 10 of the invention is identical to a conventional disk drive, an essential distinction of this tester from a disk drive is that the head positioning system is based on the use of a linear Hall-effect sensor and of a permanent magnet which is a part of a voice-coil motor.

A Hall-effect consists in that an electric field is generated in a conductor which is transverse to both the current driven through the conductor and a magnetic field applied to the conductor externally.

FIG. 2 illustrates start-stop tester 10 in a schematic, partially in a block-diagram form, in combination with the elements of an electric circuit. In this drawing, a Hall-effect sensor 42 is attached to voice coil 28, and a permanent magnet 44 is attached to housing 12 under voice coil 28 so that it can magnetically interact with voice coil 28. As is known, in a conventional disk drive, as well as in start-stop tester 10, voice coil 28 is moved with respect to stationary permanent magnet 44 under effect of a magnetic field generated by voice coil 28 when a current flows through the winding (not shown) of this coil. This movement is caused by interaction of the aforementioned magnetic field of voice coil 28 with the magnetic field of permanent magnet 44. The magnetic field of permanent magnet 44 is much stronger than that of voice coil 28 to the extent that the latter may be neglected. Each angular position of voice coil 28, and hence of pivot arm 20 which is on the other end of pivot arm, corresponds to a current value of the intensity of the magnetic field induced by permanent magnet 44. The output voltage of Hall sensor 42 is strictly proportional to this intensity. Thus, by measuring the intensity of the magnetic field generated by permanent magnet 44, it becomes possible to register any current angular position of pivot arm 20 and hence of magnetic head 24 with respect to the tracks of magnetic disk 16a.

A combined measurement and positioning system of start-stop tester 10 will now be described in more detail with reference to FIG. 2. This system, which is designated as a whole by reference numeral 46, combines two functions, i.e., accurate positioning of magnetic head 24 over magnetic disk 16a and measuring a friction force developed in contact between magnetic head 24 and magnetic disk 16a.

Measurement-positioning system 46 comprises a central processing unit (CPU) 48, which controls operation of all other units of the system and collect the data from these units, a digital-to-analog (D/A) converter 50 connected to CPU 48, a buffer amplifier 52 connected to D/A converter 50 and a close-loop positioning system 54, an analog-to-digital (A/D) converter 56 connected to CPU 48, and a scale amplifier 58 which is connected to close-loop positioning system 54. Reference numeral 55 designates a display which shows data obtained from A/D converter via CPU 48.

Close-loop positioning system 54, in turn, consists of an instrumental amplifier 60, which is located art the input of close-loop positioning system 54 and connected to a voltage-to-current converter 62, and an assembly of voice coil 28, Hall-effect sensor 42, and permanent magnet 44. Scale amplifier 58 is connected to an output of instrumental amplifier 60, and output of voltage-to-current converter 62 is connected to an input of voice coil 28.

Operation of spindle-motor unit 14, which rotates disk pack 16, is controlled by means of a motor controller 64 which is connected on one side to CPU 48 and on the other side to windings of spindle motor unit 14.

Start-stop tester 10 operates in the following manner. A housing cover (not shown) of start-stop tester 10 is removed from housing 12, and disk 16a or disk pack 16 is installed onto the spindle of spindle-motor unit 14 and is secured in place by means of washer 15 and screws 17a, 17b, 17c, and 17d. It is understood that prior to installation of disk pack 16 pivot arm 20 is shifted by a command from CPU 48 to close-loop positioning system to a position out of the disk contours shown by dash-and-dot lines in FIG. 1. After installation of disk pack 16, the cover of housing 12 is placed to close the housing and thus to provide inside the interior of housing 12 of the tester the same environment as exists inside a real disk drive.

CPU 48 sends a command to motor controller 64 to start and speed up spindle-motor 14. When spindle motor 14 reaches the rotation speed sufficient to develop an air cushion between magnetic head 24 and disk 16a, CPU 48 sends a digital positioning signal S1 to D/A converter 50 which converts this signal into an analog signal S2. The latter is sent to buffer 52 which may amplify this signal and sends the amplified signal S3 to instrumental amplifier 60. On the other hand, each position of voice coil 28 corresponds to a predetermined voltage signal S4 on the output of Hall-effect sensor 42. In the case there is a difference between signal S3 and signal S4, an error signal S5 appears on the output of instrumental amplifier 60. The latter subtracts signal S4 from signal S3, and the signal difference, i.e., error signal S5 is sent to voltage-to-current converter 62. Error signal S5 generates a current in voice coil 28. This current, in turn, generates a magnetic field proportional to error signal S5, so that voice coil 28 is shifted to a position where error signal S5 becomes equal to 0. Thus the positioning of voice coil 28 and hence of magnetic head 24 with respect to disk 16a is performed. In contrast to a disk drive, start-stop tester 10 of the invention does not use magnetic servo signals prerecorded on the disk for positioning the head with respect to the disk, but rather utilize signals sent from a source external with respect to the disk.

At first, magnetic head 24 is moved to loading zone 32 since prior to testing magnetic head may be located outside the periphery of magnetic disk 16a, and since loading zone 32 is located close to the disk center.

For the purpose of start-stop testing, after positioning of magnetic head 24 in loading zone 32, spindle-motor 14 is stopped. In order to simulate starting of a disk drive and to measure a friction force between magnetic head 24 and the surface of disk 16a in loading zone 32, spindle-motor 14 is started again. Since in start-stop tester the starting is initiated with the head 24 resting on the surface of disk 16a without any air cushion between them, i.e., from the position of the disk at rest, a friction force F is inevitably occurred between magnetic head 24 and disk 16a. This condition is shown in more detail in FIG. 3. As can be seen from this drawing, the resulting friction force F can be separated into a component F1 which is coaxial with the longitudinal axis X—X of pivot arm 20 and a component F2 which is perpendicular to longitudinal axis X—X. This component F2 develops a momentum M=F·L1, where L1 is a distance between the center O1 of magnetic head 24 and a center O2 of rotation of pivot arm 20. The momentum M tends to shift pivot arm 20 and hence head 24 from its correct position. This displacement causes generation of error signal 5, which, in turn, creates a current in the winding of voice coil 28. This current generates a magnetic field which interacts with the magnetic field of permanent magnet 44. As a result, a force Fvc is applied to voice coil 28 which resists to momentum M. Thus a force couple is developed which tends to keep pivot arm 20 fin its correct position. This condition can be expressed by the following formulae:

$$F_{VC}=K_1 \cdot I_{VC}=K_1 \cdot K_2 \cdot S5,$$

Where $I_{VC}$ is a voice-coil current, $K_1$ is a coefficient of proportionality between the voice-coil current $I_{VC}$ and force $F_{VC}$, and $K_2$ is a voltage-to-current conversion coefficient. The following equations can be written from simple geometrical dependencies:

$$F2=F \cdot \tan \alpha$$

$$F_{VC} \cdot L2 = F2 \cdot L1 = F \cdot L1 \cdot \tan \alpha$$

$$F=(L2/L1) \cdot [(K1 \cdot K2) \cdot S5]/\tan \alpha = K \cdot S5/\tan \alpha,$$

where α is an angle between longitudinal axis X—X of pivot arm 20 and the resulting friction force F. In other words, it can be seen that S5 is linearly proportional to F. Since α is known from the current position of magnetic head 24, the value of F can be calculated from the last formula. The results of these calculations of force F, as well as a current position of magnetic head 24, and any other data required for analysis of the results of the test are indicated on display 55.

The friction conditions are measured until disk 16*a* accelerates to the extent that an air cushion is formed between the disk and head 24, so that friction between both elements almost disappears. At this point, a command is sent to motor control 64 to stop spindle-motor unit, the spindle and hence disk 16*a* are stops, and the test cycle is repeated.

The aforementioned test cycles are repeated to a required number, e.g., until disk 16*a* or magnetic head 24 is severely damaged to the extent that further testing becomes meaningless.

If it is necessary to measure the viscous friction between magnetic head 24 and the surface of magnetic disk 16*a* with he presence of the air cushion between the head and the disk, the procedure is the same as in the case of physical friction with the exception that the friction force has a much lower magnitude.

Since positioning of magnetic head 22 in start-stop tester 10 does not depend on servo signals written on magnetic disk 16*a*, deterioration of the disks and heads does not affect operation of the positioning and measurement system. This means that the test can be continued till complete crash of the disk or head. Another advantage of independence of the positioning and measuring system on the physical condition of the disk and head consists in that the head can be placed into any required position between the start and stop operations for recording any test signals on the disk, or for reading any data required. Furthermore, in contrast to conventional testers, the entire disk pack or head stack can be tested as a separate or individual product. This is because in a conventional tester a strain gage is installed between each individual pivot arm and the magnetic head, so that each disk/head should be tested and measured individually. In the tester of the invention, the heads and disks can be tested individually or the whole disk pack/head stack can be considered as a product that failed the test if at least one of the disks or heads did not pass the test.

Although the invention has been described in detail with reference to a specific embodiment, it is understood that this embodiment is given only as an example, and that any modifications and changes are possible without departure from the scope of the appended claims. For example, permanent magnet 44 may be located outside housing 12 rather than inside housing 12, the tester may be constructed without buffer 52, A/D converter 56 may be replaced by a scale-type indicator. The tester can controlled manually or can operate automatically from a program. The tester may be used for testing individual heads/disks as well as for testing the head stack/disk packs. Tester 10 can be used for accurate weighing, instead of measuring a friction force, provided the tester is turned into a position perpendicular to the plane of the drawing and an object, which has to be weighed, is suspended to the tip of pivot arm. The housing of thew start-stop tester not necessarily should be the same as in the disk drive but may have an arbitrary configuration.

What is claimed is:

1. A method for testing magnetic heads and hard disks, comprising the steps of: providing a tester which has a housing for supporting a spindle motor, that holds at least one magnetic disk for rotation therewith, and a voice coil motor having a voice coil with a pivot arm for supporting at least one magnetic head magnetically interacting with said at least one magnetic disk, and a permanent magnet for interacting with said voice coil; attaching a Hall-effect sensor to said voice coil for interacting with said permanent magnet; testing at least one of test objects selected from a group consisting of said at least one magnetic disk and said at least one magnetic head by utilizing said Hall-effect sensor for positioning said at least one magnetic head in a position required for testing with respect to said at lest one magnetic disk and at the same time for measuring a friction force between said at least one magnetic head and said at least one magnetic disk during rotation of said at least one magnetic disk, said testing being a start-stop testing and prior to starting rotation of said at least one magnetic disk, said at least one magnetic head rests on said at least one magnetic disk for developing a friction force during rotation of said at least one magnetic disk; providing said tester with an instrumental amplifier and voltage-to-current converter; combining said permanent magnet, said Hall-effect sensor, said voice coil, said instrumental amplifier, and said voltage-to-current converter into a close-loop positioning and measuring system; and measuring said friction force in terms of a voltage applied to said voltage-to-current converter during said start-stop testing.

2. The method of claim 1, wherein said voltage is an error signal as a difference between a voltage signal applied to said voltage-to-current converter in said position required for testing and in a position into which said hall-effect sensor was shifted under effect of said friction force.

3. The method of claim 2, wherein said housing is identical to a housing of a conventional disk drive in terms of its dimensions and shape, said spindle motor, said voice coil motor with said pivot arm, and said permanent magnet being the same as in a conventional disk drive and being placed into said housing.

4. A method for testing magnetic heads and hard disks, comprising the steps of: providing a tester which has a housing for supporting a spindle motor, that holds at least one magnetic disk for rotation therewith, and a voice coil motor having a voice coil with a pivot arm for supporting at least one magnetic head magnetically interacting with said at least one magnetic disk, and a permanent magnet for interacting with said voice coil; attaching a Hall-effect sensor to said voice coil for interacting with said permanent magnet; testing at least one of test objects selected from a group consisting of said at least one magnetic disk and said at least one magnetic head by utilizing said Hall-effect sensor for positioning said at least one magnetic head in a position required for testing with respect to said at lest one magnetic disk and at the same time for measuring a friction force between said at least one magnetic head and said at least one magnetic disk during rotation of said at least one magnetic disk, said testing being viscous friction testing, said friction force is a viscous friction force, said method further comprising the steps of: providing said tester with an instrumental amplifier and voltage-to-current converter; combining said permanent magnet, said Hall-effect sensor, said voice coil, said instrumental amplifier, said voltage-to-current converter into a close-loop positioning and measuring system; and measuring said viscous friction force in terms of a voltage applied to said voltage-to-current converter during said viscous friction testing.

5. The method of claim 4, wherein said housing is identical to a housing of a conventional disk drive in terms of its dimensions and shape, said spindle motor, said voice coil motor with said pivot arm, and said permanent magnet being the same as in a conventional disk drive and being placed into said housing.

6. The method of claim 4, wherein said voltage is an error signal as a difference between a voltage signal applied to said voltage-to-current converter in said position required for testing and a position into which said hall-effect sensor was shifted under effect of said friction force.

7. The method of claim 4, wherein said housing is identical to a housing of a conventional disk drive in terms of its dimensions and shape, said spindle motor, said voice coil motor with said pivot arm, and said permanent magnet being the same as in a conventional disk drive and being placed into said housing.

8. The method of claim 6, wherein said housing is identical to a housing of a conventional disk drive in terms of its dimensions and shape, said spindle motor, said voice coil motor with said pivot arm, and said permanent magnet being the same as in a conventional disk drive and being placed into said housing.

9. A method for start-testing magnetic head stacks which contains a plurality of magnetic heads and magnetic disk packs which contains a plurality of magnetic disks, comprising the steps of: providing a start-stop tester which has a housing for supporting a spindle motor, that holds and rotates said magnetic disk pack, and a voice coil motor having a voice coil with a pivot arm for supporting said magnetic heads magnetically interacting with said magnetic disks, and a permanent magnet for interacting with said voice coil; attaching a Hall-effect sensor to said voice coil for interacting with said permanent magnet; testing at least one of test objects selected from a group consisting of said magnetic disk pack and said magnetic head stack by utilizing said Hall-effect sensor for positioning said magnetic heads in a position required for testing with respect to said magnetic disks and at the same time for measuring a friction force between said magnetic heads and said magnetic disks during rotation of said magnetic disk pack, said magnetic heads resting on said magnetic disks for developing friction forces during rotation of said magnetic disk pack; providing said tester with an instrumental amplifier and voltage-to-current converter; combining said permanent magnet, said Hall-effect sensor, said voice coil, said instrumental amplifier, and said voltage-to-current converter into a close-loop positioning and measuring system; and measuring said friction forces in terms of a voltage applied to said voltage-to-current converter during said start-stop testing.

10. The method of claim 9, wherein said voltage is an error signal as a difference between a voltage signal applied to said voltage-to-current converter in said position required for testing and a position into which said Hall-effect sensor was shifted under effect of said friction forces.

11. The method of claim 9, wherein said housing is identical to a housing of a conventional disk drive in terms of its dimensions and shape, said spindle motor, said voice coil motor with said pivot arm, and said permanent magnet being the same as in a conventional disk drive and being placed into said housing.

12. An apparatus for testing magnetic heads and hard disks, comprising: housing means; rotating means installed in said housing means for rotatingly supporting at least one magnetic disk; magnetic head support means for supporting at least one magnetic head interacting with said at least one magnetic disk; a combined positioning and measuring system for positioning said at least one magnetic head with respect to said at least one magnetic disk into a position required for testing and at the same time for measuring a friction force between said at least one magnetic head and at least one magnetic disk, said combined positioning and measuring system comprising a voice coil motor installed in said housing and having a voice coil with a pivot arm for supporting said at least one magnetic head and a permanent magnet for interacting with said voice coil, a Hall-effect sensor attached to said voice coil for interacting with said permanent magnet; and an instrumental amplifier and voltage-to-current converter; said permanent magnet, said Hall-effect sensor, said voice coil, said instrumental amplifier, and said voltage-to-current converter being combined into a close-loop system; friction forces between said at least one magnetic head and said at least one magnetic disk being measured on the basis of a voltage applied to said voltage-to-current converter during said start-stop testing.

13. The apparatus of claim 12, wherein said combined positioning and measuring system comprises:
a voice coil motor installed in said housing and having a voice coil with a pivot arm for supporting said at least one magnetic head and a permanent magnet for interacting with said voice coil; and
a Hall-effect sensor attached to said voice coil for interacting with said permanent magnet.

14. The apparatus of claim 13, wherein said combined positioning and measuring system further comprises:
an instrumental amplifier and voltage-to-current converter; said permanent magnet, said Hall-effect sensor, said voice coil, said instrumental amplifier, and said voltage-to-current converter being combined into a close-loop system; friction forces between said at least one magnetic head and said at least one magnetic disk being measured on the basis of a voltage applied to said voltage-to-current converter during said start-stop testing.

15. The apparatus of claim 12, wherein said voltage is an error signal as a difference between a voltage signal applied to said voltage-to-current converter in said position required for testing and a position into which said Hall-effect sensor was shifted under effect of said friction forces.

16. The apparatus of claim 12, wherein said housing is identical to a housing of a conventional disk drive in terms of its dimensions and shape, said spindle motor, said voice coil motor with said pivot arm, and said permanent magnet being the same as in a conventional disk drive and being placed into said housing.

17. The apparatus of claim 16, wherein said positioning and measuring system further comprises display means for indicating a friction force between said at least one magnetic head and said at least one magnetic head on the basis of a difference between a voltage signal applied to said voltage-to-current converter in a position required for testing and in a position into which said Hall-effect sensor was shifted under effect of said friction force.

18. The apparatus of claim 17, wherein said housing is identical to a housing of a conventional disk drive in terms of its dimensions and shape, said spindle motor, said voice coil motor with said pivot arm, and said permanent magnet being the same as in a conventional disk drive and being placed into said housing.

19. A start-stop tester for testing magnetic head stacks having a plurality of magnetic heads and magnetic disk packs having a plurality of magnetic disks comprising:

a closed and sealed housing;

a spindle motor installed in said housing for rotatingly supporting said magnetic disk pack;

means for supporting said magnetic head stack with pivotal movements with respect to said magnetic disk pack; and a combined positioning and measuring system for positioning said magnetic heads with respect to said magnetic disks into a position required for testing and at the same time for measuring a friction force between said magnetic head and said magnetic disks, said combined positioning and measuring system comprising:

a voice coil motor installed in said housing and having a voice coil with a pivot arm for supporting said at least one magnetic head and a permanent magnet for interacting with said voice coil;

a Hall-effect sensor attached to said voice coil for interacting with said permanent magnet;

an instrumental amplifier and voltage-to-current converter; said permanent magnet, said Hall-effect sensor, said voice coil, said instrumental amplifier, and said voltage-to-current converter being combined into a close-loop system; friction forces between said at least one magnetic head and said at least one magnetic disk being measured on the basis of a voltage applied to said voltage-to-current converter during said start-stop testing.

20. The apparatus of claim 19, wherein said voltage is an error signal as a difference between a voltage signal applied to said voltage-to-current converter in said position required for testing and a position into which said Hall-effect sensor was shifted under effect of said friction forces.

21. The apparatus of claim 19, wherein said spindle motor, said voice coil motor with said pivot arm, and said permanent magnet being the same as in a conventional disk drive and being placed into said sealed housing.

22. The apparatus of claim 21, wherein said positioning and measuring system further comprises:

a display means for indicating a friction force between said at least one magnetic head and said at least one magnetic head on the basis of a difference between a voltage signal applied to said voltage-to-current converter in a position required for testing and in a position into which said Hall-effect sensor was shifted under effect of said friction force;

a spindle controller connected to said spindle motor for controlling its operation;

and a central processing unit for controlling operation of said combined positioning and measuring system, said motor controller, and said display means.

* * * * *